United States Patent [19]
Elsenga-Boersma et al.

[11] Patent Number: 6,046,383
[45] Date of Patent: Apr. 4, 2000

[54] CYTOPLASMIC MALE STERILE *BRASSICA OLERACEA* PLANTS WHICH CONTAIN THE POLIMA CMS CYTOPLASM AND ARE MALE STERILE AT HIGH AND LOW TEMPERATURES

[75] Inventors: Annemarie Elsenga-Boersma, Dronten; Fransiscus Gerardus Jacobus Maria Van Den Bosch, Kesteren, both of Netherlands

[73] Assignee: Seminis Vegetable Seeds, Inc., Saticoy, Calif.

[21] Appl. No.: 09/029,709
[22] PCT Filed: Sep. 11, 1995
[86] PCT No.: PCT/US95/11497
  § 371 Date: Mar. 6, 1998
  § 102(e) Date: Mar. 6, 1998
[87] PCT Pub. No.: WO97/09873
  PCT Pub. Date: Mar. 20, 1997
[51] Int. Cl.[7] .............................. A01H 1/02; A01H 5/00; A01H 5/10; C12N 15/05
[52] U.S. Cl. .......................... 800/274; 800/268; 800/269; 800/277; 800/298; 800/303; 800/304; 800/306; 435/421; 435/430; 435/453
[58] Field of Search ................................... 800/274, 268, 800/277, 269, 298, 303, 304, 306; 435/453, 421, 430

[56] References Cited

U.S. PATENT DOCUMENTS 5,254,802  10/1993  Hoekstra et al. ...................... 800/220

OTHER PUBLICATIONS

Sodhi, et al., Identification of a Stable Maintainer Line for Polima Cytoplasmic Male Sterility in Rapeseed (*B.napus* L.), *Plant Breeding*, 110:334–337, (1993).

Fan et al. 1986. Can. J. Plant Sci. 66:221–227.

Yarrow et al. 1990. Plant Cell Reports 9:185–188.

Barsby et al. 1987. Plant Science 53:243–248.

Dong, F. 1981. Encarpia Crucifera Newsletter 6:6–7.

*Primary Examiner*—David T. Fox
*Attorney, Agent, or Firm*—Rockey, Milnamow & Katz, Ltd.

[57] ABSTRACT

The present invention involves cytoplasmic male sterile *Brassica oleracea* plants that contain polima CMS cytoplasm. The plants remain sterile at high temperatures. The *Brassica oleracea* plants of the present invention can be prepared by traditional breeding techniques. Different Brassica types can then be produced using these plants by employing traditional breeding techniques or by protoplast fusion.

12 Claims, 2 Drawing Sheets

CYTOPLASMIC MALE STERILE BRASSICA OLERACEA PLANTS WHICH CONTAIN THE POLIMA CMS CYTOPLASM AND ARE MALE STERILE AT HIGH AND LOW TEMPERATURES

This application is a 371 of PCT/US95/11497 filed Sep. 11, 1995.

FIELD OF THE INVENTION

The present invention involves cytoplasmic male sterile *Brassica oleracea* plants that contain polima CMS cytoplasm, are male sterile at high and low temperatures, and exhibit good female fertility.

BACKGROUND OF THE INVENTION

In an effort to increase the productivity of plants and food crops, plant breeders generally develop cultivars that contain certain desirable characteristics such as increased height, growth rate, higher yields, etc. One of the ways in which this may be accomplished is by infusing desirable characteristics into a plant to form a superior plant line. Superior lines are then combined to form an $F_1$ hybrid that contains the desirable characteristics. Such superior hybrids can be developed in numerous ways.

One popular way of producing superior hybrids is by using male sterility in one of the plants for which hybridization is desired. Male sterile lines allow the breeder to produce hybrid seed more economically by controlling cross-fertilization in the flower of a plant. Cross-fertilization can be controlled by preventing the female parent from self fertilizing. Self-fertilization is eliminated by making the plant male sterile. If the plant is male sterile, then no pollen can be produced for fertilization. Once rendered male sterile, the plant may then be hybridized with a gene donor plant possessing the desired characteristics.

One way to effectuate male sterility is through the use of cytoplasmic male sterility. Present belief is that genetic factors controlling cytoplasmic male sterility (CMS) are found in the cytoplasm, particularly in the genes of the mitochondrial DNA.

Three of the most common cytoplasmic male sterilities in the Brassica species are:

1) Ogura male sterile cytoplasm of *Raphanus sativus;*
2) Polima male sterile cytoplasm of *Brassica napus;* and
3) Nap male sterile cytoplasm of *Brassica napus.*

In Brassica, cytoplasmic male sterility can be transmitted by crossing. The female (egg) parent contributes the cytoplasm, therefore, crossing to CMS females produces CMS progeny. The nuclear genes however are heterozygous. Therefore, six to eight generations of "backcrossing" are necessary to produce a CMS line breeding homozygous for nuclear characters. As an alternative, cytoplasmic male sterile lines can also be produced by protoplast fusion. In protoplast fusion, a protoplast from a plant having commercially desirable traits is combined with a protoplast of a CMS line. The nuclear material of the CMS line is either removed or inactivated prior to fusion so it donates only the cytoplasm. The resulting cytoplasmic hybrid (or cybrid) possesses the CMS cytoplasm and is male sterile. For example, U.S. Pat. No. 5,254,802 discloses *B. oleracea* plants that contain the Ogura CMS cytoplasm. These plants were obtained by protoplast fusion.

Polima CMS cytoplasm has been used to produce CMS in varieties such as winter-type oil seed rape (*Brassica napus*) (See Barsby et al., *Plant Science*, 53: 243–248 (1987)). However, one significant problem with the expression of cytoplasmic male sterility by the polima CMS cytoplasm is that the polima cytoplasm is influenced by environmental conditions. Fan, Z et al. *Can. J. Plant Sci.* 66:221–227 (1985). More specifically, male sterile plants containing polima CMS cytoplasm are known to become fertile under high temperatures in the field. Id. See also Fu, T. D., *Encarpia Cruciferea Newsletter* 6: 6–7 (1981).

SUMMARY OF THE INVENTION

The present invention involves *Brassica oleracea* plants that contain Polima CMS cytoplasm which remain male sterile at high and low temperatures and exhibit good female fertility. The *Brassica oleracea* plants of the present invention can be produced by traditional breeding methods. Different Brassica types can then be developed by further crossings or backcrossings or by protoplast fusion.

To obtain the *Brassica oleracea* plants of this invention by traditional breeding techniques, an interspecific cross was made between *Brassica campestris* cultivar 87110 and *Brassica oleracea* cultivar 87101. The seeds resulting from the cross are collected, planted and regenerated. The resulting plants are *Brassica napus* and contain a haploid set of chromosomes. The chromosomal content of said *Brassica napus* must be doubled by treating the plants with colchicine.

A second interspecific cross is performed by crossing *Brassica campestris* cultivar 87118 with *Brassica oleracea* cultivar 87101. The seeds resulting from the cross are collected, planted and regenerated. As in the previous cross, the resulting plants are *Brassica napus* and contain a haploid set of chromosomes. The plants are treated with colchicine to double their chromosome content.

The *Brassica napus* plants produced as a result of the second interspecific cross are next crossed with a *Brassica napus* cultivar 87102, which contains polima CMS cytoplasm and is male sterile. The seeds resulting from the cross are collected, planted and regenerated. The regenerated plants are *Brassica napus* and contained the polima CMS cytoplasm.

The resulting plants are subsequently crossed with the *Brassica napus* plants produced as a result of the first interspecific cross. The seeds resulting from the cross are collected, planted and regenerated. The regenerated plants are *Brassica napus*, contain the Polima CMS cytoplasm and are male sterile.

The resulting plants are then crossed with a normal *Brassica oleracea*. As a result of the cross, siliques are produced, collected and examined for seeds. The seeds are collected for embryo rescue, because typically, embryos produced from such interspecific hybridization abort prior to maturation. However, by employing embryo rescue techniques, interspecific hybrid plants can be produced. The resulting $F_1$ plants contain the polima CMS cytoplasm from the female *Brassica napus*, however; the nuclear DNA content is a combination of the *Brassica napus* (N=19) and the *Brassica oleracea* (N=9).

The resulting plants are then backcrossed with a *Brassica oleracea*. Siliques are again produced, collected and examined for seeds. The seeds are collected for embryo rescue. The embryos are then regenerated as in the previous cross. The resulting plants are intermediate for chromosome number and contain the polima CMS cytoplasm. The nuclear content of the plants is a combination of *Brassica napus* and *Brassica oleracea*.

The resulting plants are then backcrossed with *Brassica oleracea*. Siliques are again produced, collected and examined for seeds. The seeds are sown. The resulting plants are *Brassica oleracea* which are male sterile and contain the polima CMS cytoplasm.

Optionally, the male sterile *Brassica oleracea* plants may be further crossed or backcrossed to produce different *Brassica types*. Siliques will again be produced, collected and examined for seeds. The seeds are sown. The resulting plants are *Brassica oleracea* which contain the polima cytoplasm and are male sterile.

Different Brassica types can also be produced by protoplast fusion. A protoplast from a male sterile *Brassica oleracea* containing the polima CMS cytoplasm and inactivated nuclei is fused with a protoplast of a Brassica having commercially desirable characteristics. After the fusion, the allogenic cells are regenerated into CMS Brassica plants. The resulting plants are male sterile and contain the polima cytoplasm. The regenerated CMS Brassica plants contain the polima cytoplasm and can be employed in crossings with other Brassica types containing commercially desirable characteristics.

DETAILED DESCRIPTION OF THE INVENTION

Cytoplasmic male sterile *Brassica napus* plants containing polima cytoplasm are known to "leak". Leakiness refers to the fact that the plants tend to lose their sterility under certain temperature conditions. For example, studies have shown that CMS *Brassica napus* containing polima cytoplasm plants are only partially sterile at high temperatures. See Fan, Z et al., *Can. J. Plant Sci.* 66: 221–227 (1985).

The present invention involves CMS *Brassica oleracea* plants that contain the polima cytoplasm. The plants are male sterile at high and low temperatures and exhibit good female fertility. Different Brasica CMS types can then be developed by employing further crossings and backcrossings or protoplast fusion.

The Breeding Program

Traditional breeding techniques were used to develop the *Brassica oleracea* plants of the present invention. The inventors herewith describe the breeding program used to create the *Brassica oleracea* plants of this invention. The breeding program was undertaken by making an interspecific cross between a *Brassica campestris* (=*Brassica rapa*) entry 87110 (n=10) and a *Brassica oleracea* entry 87101 (N=19). Entry 87110 was obtained from the Centre for Plant Research (CPRO), P.O. Box 16, 6700 AA, Wageningen, The Netherlands as entry IVT 86007 paar 3MS and was genetically male sterile. 87110 has been deposited under the Budapest Treaty with the American Type Culture Collection (ATCC), 10801 University Boulevard, Manassas Va. 20110-2209. 87110 was deposited on Aug. 23, 1995 and received ATCC Accession Number 97246. Entry 87101 is available from the Crucifer Genetics Cooperative (CrGC) at the Department of Plant Pathology, 1630 Linden Drive, University of Wisconsin, Madison, Wis. as CRGC #3-3 (Ccc) and is a rapid cycling *Brassica oleracea*. After the crossing, siliques (seeds) developed. The siliques are collected, examined for seeds and planted. The resulting plants were haploid *Brassica napus* ac (N=19) and were subjected to colchicine treatment to double chromosomes to the diploid number aacc (2n=38). The resulting plants were "artificial" *Brassica napus* with an aacc genome. These were labelled 87116.

A second *Brassica campestris*, 87118, having the same characteristics as 87110, was also crossed with 87101. 87118 was received from the CPRO as IVT 86017 paar 3MS. 87118 has been deposited under the Budapest Treaty with the American Type Culture Collection (ATCC), 10801 University Boulevard, Manassas Va. 20110-2209. 87118 was deposited on Aug. 23, 1995 and received ATCC Accession Number 97247. As in the previous cross, the seeds were collected and planted. The resulting plants were subjected to colchicine treatment to double the chromosomes. The resulting plants were an "artificial" *Brassica napus* with an aacc genome. The resulting plants were labeled 87119.

Plants of 87119 were then crossed with a male sterile *Brassica napus* (aacc) containing the polima CMS cytoplasm (labeled 87102). 87102 is available from the Crucifer Genetics Cooperative as CrGC #5-4 (AClaacc) which is a rapid cycling *Brassica napus* with "Polima" CMS cytoplasm. Siliques were produced, collected and examined for seeds. The seeds were planted and the resulting plants labeled 88102. These plants were *Brassica napus*, had an aacc genome and contained the polima CMS cytoplasm.

A cross was then made between 87116 and 88102. Siliques were produced, collected and examined for seeds. The seeds were planted. The resulting plants were *Brassica napus* (aacc) and were labeled 88125. *Brassica napus* (aacc) is an amphidiploid species between *Brassica oleracea* N=9 (cc genome) and *Brassica rapa* N=10 (aa genome). 88125 are *Brassica napus* (aacc) and contains polima CMS cytoplasm and are male sterile.

An interspecific cross was made between 88125 (aacc) and a normal male fertile broccoli plant, *Brassica oleracea* (cc). One skilled in the art would recongize that any male fertile *Brassica oleracea* plant could be used for this cross. Siliques developed. The siliques were then collected and examined for seeds. If seeds were present, then the embryo(s) is/were rescued. The embryo(s) is/were rescued because typically, embryos produced from such an interspecific hybridization abort prior to maturation. However, by employing embryo rescue, interspecific hybrids can be produced.

Embryo rescue involves removing the embryo from the silique. It is preferred that the embryo rescue be conducted when the embryo is as large as possible. Generally, 18–19 days after the cross is a good time to conduct embryo rescue. However, one skilled in the art would recognize that the embryo rescue could take place earlier or later, so long as the seed coat has not yet hardened.

In embryo rescue, the siliques are first disinfected for about 20 minutes in a 10% hypochlorate solution (such as sodium or potassium hypochlorate) and rinsed three times in sterile water at 2.5 and 10 minutes.

Next, the siliques are cut in a longitudinal direction. Young seeds are removed and embryos taken out of the seed under a microscope. The embryos are then placed on a suitable medium to facilitate growth, such as a BLKC medium which is described in Example 11. However, any medium that facilitates growth can be used. The embryos are grown at 20° C. in 16 hours of 4500 LUX light for at least two weeks. After the roots develop, the seedlings are placed into soil as soon as possible.

The resulting $F_1$ plants were assigned the numbers 88132-1 through 88132-84. These plants contained the polima CMS cytoplasm from the female Brassica napus plant, however; the nuclear DNA content was a combination of the Brassica napus (N=19) and the Brassica oleracea (N=9). Essentially, the plants had mixed genomes. Because of their mixed nature, the plants were male sterile and partially female sterile. The plants were male sterile because they contained the polima CMS cytoplasm from the female (egg) parent, Brassica napus, 88125.

Phenotypical selection was used to select the plants from 88132-1 through 88132-84 that have near normal DNA content (aacc or cc). Phenotypic selection allows the breeder to select plants most similar to Brassica oleracea (cc genome). Plants with an abnormal DNA content are visually different than plants with a normal DNA content. The plants selected were backcrossed (BC1) with a normal broccoli or cauliflower, Brassica oleracea (cc). However, one skilled in the art would recognize that any Brassica oleracea could be used. After the cross, embryo rescue was again employed. The plants that developed were assigned the numbers 89015 through 89040 and 89046 through 89056. These plants were intermediate for chromosome number and contained the polima CMS cytoplasm. Again, the nuclear DNA content was a combination of the Brassica napus and the Brassica oleracea. The plants were male sterile (polima CMS) and partially female sterile (chromosome number).

Phenotypical selection was employed to select plants from 89015 through 89040 and 89046 through 89056 having near normal DNA content. The plants selected were backcrossed (BC2) with a normal broccoli or cauliflower, Brassica oleracea (cc). However, one skilled in the art would recognize that any Brassica oleracea could be used. Siliques again developed, however, some seeds did not require embryo rescue. These seeds were collected and planted. The plants resulting from this cross were assigned the numbers 89070 through 89141. Most of these plants had the normal Brassica oleracea set of chromosomes (2N=18), contained the polima cytoplasm and were male sterile. The flowers of these plants had reduced anthers and petals. The plants remained sterile at high and low temperatures and exhibited normal female fertility.

These resulting plants can be crossed with other Brassica types such as broccoli, cauliflower, cabbage (red, white, savoy), brussels sprouts, kohlrabi, kale, etc. to produce CMS lines. For example, different Brassica types can be produced by backcrossing to the CMS "polima" plants or by protoplast fusion.

Subsequent Crosses and Selection Process for Male Sterility, Female Fertility and Flower Morphology Plants of 89015 through 89640 and 89046 through 89056 and 89070 through 89141 were subsequently backcrossed with a normal broccoli and/or cauliflower and planted in the field. Siliques developed, were collected and examined for seeds. The seeds were collected and then sown. Rows of polima steriles were alternated with broccoli maintainer rows. A maintainer line is understood by those of ordinary skill in the art to denote a line that is used in crosses to produce progeny that maintain the sterility of the male sterile material parent. The maintainer plants are fertile but otherwise genetically identical counterparts to the CMS plants with which they are grown, typically in alternating strips, to produce seed from a male-sterile line. After a period of growth, natural selection (by bees/flies, etc.) was employed to choose the plants exhibiting male sterility, good female fertility and the best flowers morphology, i.e. good petal size. The plants selected were assigned numbers CPO-1, -2, etc. These plants were Brassica oleracea, contained the polima CMS cytoplasm were male sterile and exhibited good female fertility.

After a period of growth, the CPO numbered plants exhibiting male sterility, good female fertility were cloned and put in a cage with a typical maintainer. Cage production involves erecting a mesh tent (insect screening) or a cage around the plants. This is done to prevent cross pollination by insects with other plants in the field. A beehive or other insect colony is typically put inside with the plants. Siliques that developed were collected and the seeds sown. The resulting plants were Brassica oleracea which contained the polima CMS cytoplasm, were male sterile and exhibited good female fertility.

Protoplast Fusion

Different CMS Brassica types can also be prepared by protoplast fusion. The protoplasts can be obtained from a Brassica oleracea plant that contains the CMS polima cytoplasm and is male sterile. For example, Brassica oleracea plants obtained by the previously described breeding program can be used, such as plants of 89070 through 89111 and plants of the CPO series. The protoplast fusion may be accomplished by employing polyethylene glycol (PEG) causing agglutination, in the presence of a fusion buffer, i.e. a high pH solution to let the membranes fuse. Such somatic hybridization may be effected under the conditions disclosed by Sundberg et al. (Plant Science 43 (1986) 155), hereby incorporated by reference, for the production of interspecific hybrids or modifications thereof. However, one skilled in the art would recognize that the protoplast fusion can be accomplished in other ways other than using polyethylene glycol (PEG). For example, the protoplasts can be fused by using electric field-induced fusion techniques as described by Koop et al. "Electric Field-Induced Fusion and Cell Reconstruction-with Preselected Single Protoplasts and Subprotoplasts of Higher Plants" in Electroporation and Electrofusion in Cell Biology, Neuman et al. editors, pgs 355–365 (1989), herewith incorporated by reference. Additionally, protoplast fusion can be accomplished with dextran and polyvinyl alcohol as described by Hauptmann et al., "Carrot x Tobacco Somatic Cell Hybrids Selected by Amino Acid Analog Resistance Complementation", 6th International Protoplast Symposium, Basel, Aug. 12–16, 1983, herewith incorporated by reference.

If protoplast fusion is to be accomplished with polyethylene glycol, the procedure described below can be used.

The protoplast fusion is conveniently effected in a washing solution (W5'), described below, containing an osmoticum e.g. a carbohydrate such as mannitol, sorbitol, glucose, or sucrose and potassium and calcium salts. The pH can range from 5.2 to 10 and is preferably about 5.7. The protoplasts of different origin are mixed and concentrated, conveniently to a final density of $10^5$ and $10^8$ protoplasm per ml.

The protoplast mixture should then be left undisturbed for at least 10 minutes to allow the protoplasts to settle at the bottom of the petri dish. The mixture is then treated with polyethylene glycol (PEG), preferably having a molecular weight of 1500 to 6000. In general, good results are obtained when employing an aqueous solution (PFS) comprising 18.8% by weight of PEG at a volume ratio W5' to PFS of 10:1 to 1:1. PFS comprises conveniently an osmoticum and a calcium salt. The protoplasts are included in PFS for 15 to 20 minutes depending on the fragility of the cells.

The fusion is accomplished by washing the protoplasts, for example, three times, with washing solution (W5') containing an osmoticum (e.g. glucose) in a concentration giving a lower osmolarity than PFS and potassium, sodium and calcium salts. The fusion procedure is carried out at a temperature in the range between 16° and 20° C., preferably 18° C. The concentration of PEG in the fusion mixture is gradually decreased with each consecutive washing step (see e.g. Example 6). Each washing step should take at least 5 minutes to allow the protoplasts to adjust slowly to the lower osmolarity of the medium, to avoid bursting of the cells. After the washing steps have been accomplished the fused protoplasts should be in the range of $10^5$ to $10^6$ protoplasts per ml. The obtained fusion products may be regenerated in the presence of non-fused parental protoplasts or after optical selection from the culture. Such optical selection may be performed by micro-manipulation of the cells, e.g. according to the procedure disclosed by Patnaik et al., *Plant Science Letters* 24 (1982) 105, hereby incorporated by reference, for the manual isolation and identification of plant heterokaryon.

When employing the selection strategy, the parental protoplasts are for example stained with fluorescent dyes, e.g. fluorescein diacetate. When fluorescein diacetate is used with protoplasts of hypocotyl origin it will stain yellow under a UV light. Protoplasts from leaves will contain chloroplasts which give red auto-fluorescence under UV light.

The obtained fusion products are cultivated in an appropriate culture medium comprising a well-balanced nutrient supply for protoplast growth. The medium contains micro- and macro-elements, vitamins, amino acids and small amounts of carbohydrates, e.g. various sugars such as glucose. Glucose serves as a carbon source as well as an osmoticum. The culture medium also comprises plant hormones (auxins and cytokine) which are able to regulate cell division and shoot regeneration. Examples of suitable auxins include naphtyl acetic acid (NAA), 2,4-dichlorophenoxyacetic acid (2,4-D) and indoleacetic acid (IAA). Examples of suitable cytokinins include benzyl aminopyrine (BAP), zeatin (Zea) and gibberellic acid (GA3). In general NAA and 2,4-D are used in combination with BAP to initiate cell division. The ratio of auxin/cytokinin must then be high, for example greater than 1. Two or three days after the fusion treatment, the medium is largely replaced by culture medium (BP) which comprises agarose, by which the fusion products and the parental protoplasts are embedded.

After 14 days, the concentration of auxins is diluted by addition of other culture media containing no or substantially less auxins. Star-shaped micro calli will generally develop after 3 to 4 weeks. Such micro calli are then transferred to a regeneration medium to initiate shoot formation, preferably after adaption in an intermediate regeneration medium to differences in composition and physical properties between the culture medium and the regeneration medium. For shoot formation the ratio auxin/cytokinin in the regeneration medium should conveniently be low, e.g. below 1:10. In general it will be preferable to employ the auxin NAA in combination with the cytokinins Zea and BAP for shoot regeneration. The regeneration media, BR and K3, are relatively poor media compared to the culture medium. They contain less vitamins, the content of carbon source is lower, they comprise solely sucrose and xylose as carbon source and do not contain amino acids. The regeneration media also have a higher viscosity that the culture medium. The regeneration medium Br is a solid medium and contains the growth regulators 2,4-D, NAA and BAP, with the ratio of auxin to cytokinin being less than 1. Medium K3 contains Zea, GA3 and also silver nitrate to promote the shoot development.

After two weeks regeneration on Br medium, calli of approximately 3 mm in diameter are transferred to K3 regeneration medium containing a low sucrose concentration. At this stage shoots will develop within 2 to 3 weeks. The obtained shoots are then rooted on a basic medium, such as B5, without additional hormones. The nuclear DNA and mitochondrial DNA of the obtained plantlets may then be identified in a manner known per se, e.g. employing suitable restriction endonuclease and comparing the thus obtained DNA digest pattern of the fusion products with that of the parental lines.

*Brassica oleracea* protoplasts and inactivated protoplasts of a Polima CMS *Brassica oleracea* plant, employed herein as starting material may be obtained in a manner known per se from the corresponding plant cells. Cell wall-free cells, i.e. protoplasts are obtained from green plant material e.g. leaf material and from white plant material e.g. etiolated seedlings, according to the method disclosed by Glimelius, *Physiologia Plantarum* 61 (1984) 38, hereby incorporated by reference, for the regeneration of hypocotyl protoplasts. Where optical selection of the fusion products is intended, the starting materials will be conveniently selected from a green plant or where they are from white-plant material they will advantageously be stained to facilitate selection. The inactivated protoplasts of a Polima CMS *Brassica oleracea* plant are obtained in a manner known per se corresponding to Polima CMS *Brassica oleracea* plant cells or protoplasts, for example, by irradiation.

The inactivation of the nucleus by irradiation can be effected with the aid of gamma, UV or X-rays. Where irradiation is effected with an X-ray source, nucleus inactivation will in general be obtained by applying a dose of e.g. 10 krad. min for 3 to 20 minutes. The appropriate X-ray dosage may for example be established by determining the minimum level of X-ray irradiation killing 100% of the protoplast population: the percentage of dead cells is estimated by counting the number of formed colonies after 10 to 20 days in culture.

As described above, after the fusion, the allogenic cells are regenerated to form *Brassica oleracea* plants containing the CMS cytoplasm. These plants may be subsequently crossed with other *Brassica oleracea* plants.

It will be appreciated that the *Brassica oleracea* plant of this invention may be employed as starting material for the preparation of other *Brassica oleracea* varieties having Polima CMS by in vitro and/or crossing techniques. Such in vitro and crossing techniques are known in the art by the skilled breeder.

A. ENZYME SOLUTION (1 L)

90 g mannitol
0.0272 g $KH_2PO_4$
0.1 g $KNO_3$
0.246 g $MgSO_4 \cdot 7H_2O$
0.0008 g KI
0.00025 g $CuSO_4 \cdot 5H_2O$
1.4 g $CaCl_2 \cdot 2H_2O$
1.1 g MES
6 g Cellulose R10
1 g pH 5.8 Macarozyme

B. WASHING SOLUTIONS (W5) (1 L)

18.4 g $CaCl_2 \cdot 2H_2O$
4.91 g NaCl
0.372 g KCl
0.901 g glucose
pH = 5.8

C. WASHING SOLUTION (W5') (1 L)

18.4 g $CaCl_2 \cdot 2H_2O$
4.91 g NaCl
0.372 g KCl
0.901 g glucose 9.76 g MES
pH = 5.8

D. CPW 16 S (1 L)

160 g sucrose
0.0272 g $KH_2PO_4$
0.1 g $KNO_3$
1.45 g $CaCl_2 \cdot 2H_2O$
0.246 g $MgSO_4 \cdot 2H_2O$
0.0008 g KI
0.000025 g $CuSO_4 \cdot 5H_2O$
pH = 5.5–5.8

E. PEG fusion solution (PFS)

18.8% PEG (MW 4000)
0.06 M $CaCl_2 \cdot 2H_2O$
0.1 M mannitol
0.025 M glucine
10% (v/v) DMSO

F. SPA SOLUTION (1 L)

20 g SeaPlaque agarose
100 g Sucrose

TABLE 1

COMPOSITION OF THE MS MEDIA (MG/L)

| | 8 P | MAC | Br | K 3 | B 5 | MS |
|---|---|---|---|---|---|---|
| $KNO_2$ | 956 | 956 | 1556 | 1556 | 3000 | 1900 |
| $NH_4NO_3$ | 600 | 600 | 250 | 250 | — | 1650 |
| $MgSO_4 \cdot 2H_2O$ | 300 | 300 | 250 | 250 | 250 | 370 |
| $KH_2PO_4$ | 164 | 164 | — | — | — | 170 |
| $CaCl_2 \cdot 2H_2O$ | 600 | 600 | 300 | 300 | 150 | 440 |
| KCl | 300 | 300 | — | — | — | — |
| $(NH_4)_2SO_4$ | — | — | 134 | 134 | 134 | — |
| K | 0.75 | 0.75 | 0.75 | 0.75 | 0.75 | 0.83 |
| $MnSO_4 \cdot 4H_2O$ | 10 | 10 | 10 | 10 | 10 | 22.3 |
| $H_3BO_3$ | 3 | 3 | 3 | 3 | 3 | 6.2 |
| $ZnSO_4 \cdot 2H_2O$ | 2 | 2 | 2 | 2 | 2 | 8.6 |
| $NaMoO4 \cdot 2H_2O$ | 0.25 | 0.25 | 0.25 | 0.25 | 0.25 | 0.25 |
| $C_4SO_4 \cdot 4H_2O$ | 0.025 | 0.025 | 0.025 | 0.025 | 0.025 | 0.025 |
| $CoCl_2 \cdot 6H_2O$ | 0.025 | 0.025 | 0.025 | 0.025 | 0.025 | 0.025 |
| Fe-EDTA | 40 | 40 | 40 | 40 | 40 | 43 |
| Thiamine-HCL | 10 | 10 | 10 | 10 | 10 | 0.1 |
| Pyridoxine-HCL | 1 | 1 | 1 | 1 | 1 | 0.5 |
| Nicotinic acid | 1 | 1 | 1 | 1 | 1 | 0.5 |
| Sodium pyruvate | 20 | 20 | — | — | — | — |
| Citric Acid | 40 | 40 | — | — | — | — |
| Maleic acid | 40 | 40 | — | — | — | — |
| Furnaric acid | 40 | 40 | — | — | — | — |
| Glycine | — | — | — | — | — | 2 |
| Xylose | — | — | 250 | — | — | — |
| Inositol | 100 | — | — | — | — | 100 |
| Sucrose | 50,000 | 80,000 | 40,000 | 10,000 | 20,000 | ** |
| Glucose | 40,000 | — | — | — | — | — |
| Casein hydrolysate | 250 | 250 | — | — | — | — |
| Agarose | — | — | 16,000 | — | — | — |
| Agar | — | — | — | 8,000 | 8,000 | 8,000 |
| NAA | 0.1 | 0.1 | 0.1 | — | — | — |
| 2,4-D | 1 | 0.2 | 0.1 | — | — | — |
| Zeatin | — | — | — | 0.26 | — | — |

TABLE 1-continued

| | COMPOSITION OF THE MS MEDIA (MG/L) | | | | | |
|---|---|---|---|---|---|---|
| | 8 P | MAC | Br | K 3 | B 5 | MS |
| BAP | 0.5 | 0.5 | 0.5 | — | — | — |
| GA₃ | — | — | — | 0.006 | — | — |
| AgNO₃ | — | — | — | 5 | — | — |

** see examples

By way of example, and not limitation, examples of the present invention will now be given.

EXAMPLE 1
Seed Sterilization and Germination

Seeds of *Brassica oleracea*, broccoli with Polima CMS (hereinafter designated *B. oleracea*, 904005-1) are dipped for approximately 10 seconds in 70% alcohol and sterilized in a 1.5% sodium hypochlorite solution for two times for 10 minutes at 20° C. Afterwards extensive rinsing with sterile distilled water is required. The seeds are placed on the MS nutrient medium (see Table 1) with 3% sucrose and without hormones. To obtain green sterile plants, the seeds are grown in glass jars in the light (8000 lux), for a 16 hour photoperiod with temperatures of 25° C. day and 20° C. night. Sterile shoots are subcultured under the same conditions in plastic containers. To obtain white tissue for protoplast isolation, e.g. hypocotyls, the seeds are grown in petri dishes in the dark at 25° C.

EXAMPLE 1a
Crosses Leading to 904005-1

904005-1 is the seed harvested from plant number 1 in entry number 904005. 904005 was a backcross of CMS Polima 892731-2 and a normal fertile broccoli. 892731-2 is the seed harvested from plant selection 2 in entry 892731. This was backcross of CMS Polima 89094-2 and a normal fertile broccoli.

89094-2 is the seed harvested from plant selection 2 in entry 89094. This was a backcross of CMS Polima 89022 and normal fertile broccoli.

89022-4 is the seed harvested from plant 4 in entry 89022.

EXAMPLE 2

Analogous to the procedure of Example 1, seeds of *Brassica oleracea*, cultivar DE70, are sterilized and germinated. Cultivar DE70 is a fully fertile inbred cauliflower line that is used as a parental line. However, any typical *Brassica oleracea* plant can be used for the protoplast fusion.

EXAMPLE 3
Isolation of Protoplasts

Leaves of four week old shoots of plant material according to Example 1 are cut into small pieces and incubated in an enzyme solution for 16 hours at 25° C. on a gyratory shaker at 40 rpm. The suspension is filtered through a nylon mesh (40 µm) and washed with two-thirds of a volume of CPW 16S solution by centrifugation at 817 rpm for 5 minutes. This results in flotation of the intact protoplasts. The protoplasts are collected and rinsed twice with W5 solution by centrifugation at 708 rpm for 5 minutes. The protoplasts are diluted to a density of $1 \times 10^5$ protoplasts per ml W5 solution before being used for fusion experiments.

EXAMPLE 4

Six to eight day old hypocotyls of the plant material according to Example 2 are isolated according to the process of Example 3, except that during the enzyme treatment 3 µg/ml of fluoresceinediacetate is added. Stained protoplasts for hand selection and for determination of fusion frequency are obtained.

EXAMPLE 5
Irradiation of Protoplast

Freshly isolated protoplasts according to Example 3 are plated in a 6 cm petri dish in W5 solution (2 to 3 ml). The protoplasts are irradiated using an X-ray source (Baltograph CE100), at a dose of 3500 Gy during 20 minutes. After irradiation, the inactivated protoplasts are washed with W5 solution by centrifugation at 708 rpm for 5 minutes. The protoplasts are diluted to a density of $1 \times 10^5$ protoplasts per ml W5 solution before being used for fusion experiments.

EXAMPLE 6
Fusion Procedure

Protoplasts according to Example 4 and 5 re mixed 1:3 in a final concentration of $1 \times 10^5$ protoplasts per ml W5 solution. Three droplets of 100 µl are placed in an uncoated 6 cm petri dish and the protoplasts are allowed to settle for 5 to 10 minutes. Three hundred microliters of PFS solution is added in the center of the three droplets to induce agglutination for 15 minutes. Thereafter, 300 µl of W5 solution is added to the mixture and again after 10 minutes and again after 5 minutes. The W5 medium is replaced by two times concentrated 8P solution and the protoplasts are cultivated for one to three days at 25° C. in the dark.

EXAMPLE 7

The entire fusion mixture according to Example 6 is cultured for one to three days in the dark at 25° C. The cells are collected by centrifugation at 548 for 5 minutes and diluted to a density of $1 \times 10^5$ protoplasts per ml two times concentrated 8P medium. An equal volume handwarm SPA medium is added and the cells are plated in 5 droplets of 100 µl in a coated petri dish. Also 5 droplets of 100 µl with feeder cells are added. After two weeks, the droplets with feeder cells are removed and 2 ml MAC medium per petri dish is added. After two weeks the droplets are dispersed on solid Br medium. After two to three weeks the individual colonies are transferred to a petri dish with solid K3 medium. The microcalli are cultured in low light intensity (2500 lux) at 25° C. with a photoperiod of 18 hours.

EXAMPLE 8
Selection and Growth of Fusion Products

Fused cells, which can be recognized visually by the presence of double fluorescence, are picked up with a micromanipulator. The hybrid cells are cultured in 100 µl agarose droplets (1% SeaPlaque) at a density of 2000 to 50,000 protoplasts per milliliter. The droplets are placed in a liquid nurse culture system (Costar-Transwell col) with feeder cells and incubated at 25° C. in the dark. The droplets are dispersed on solid Br medium after two weeks. Small calli are transferred to solid K3 medium and incubated at 25° C. in low light intensity (2500 lux) with a photoperiod of 16 hours.

EXAMPLE 9
Plant Regeneration

The calli according to Example 7 and 8, having developed to a size of 2 to 5 mm in diameter, are transferred to fresh K3 medium at normal light intensity (8000 lux) at 25° C. with a photoperiod of 16 hours. Small shoots are transferred to B5 medium with 1% sucrose without hormones and rooted on the same medium.

Figure 1:
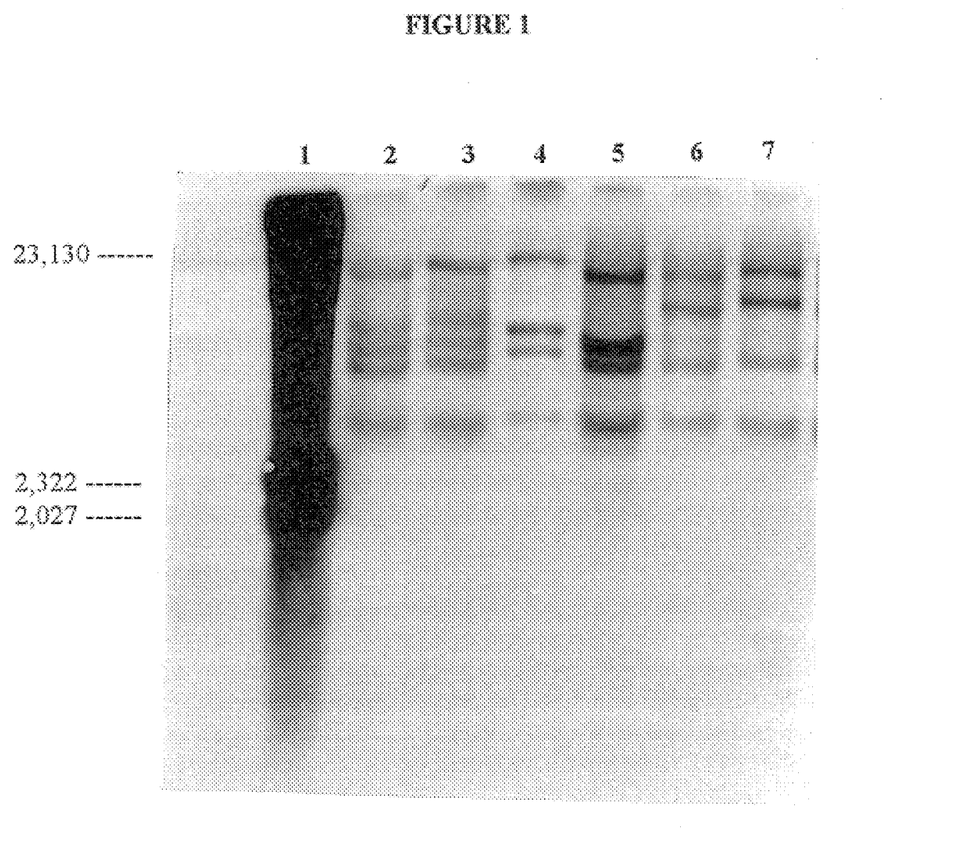
FIG. 1 shows the different hybridization patterns of BGL I digested DNA with probe E5 in an endonuclease digest containing nuclear DNA of a polima CMS donor, *Brassica oleracea* 904005-1, and *Brassica oleracea* breeding lines used as acceptors for the CMS trait. Lane 1 shows Phage λ Hind III digested DNA Fragments (MW Standards). Lanes 2 and 3 show Polima CMS *Brassica oleracea* 904005-1 DNA. Lanes 4 and 5 show *Brassica oleracea* acceptor Line K14. Lanes 6 and 7 show *Brassica oleracea* acceptor Line DE70.

EXAMPLE 10
Molecular Analysis of the Fusion Products a) Nuclear DNA composition Characterization of the nuclear DNA composition of the fusion product is effected by using specific DNA probes. Probe ES, a clone containing a 820 kbp Bgl 1 fragment from cauliflower nuclei DNA hybridizes with various bands in an endonuclease digest pattern of nuclear DNA of the Polima CMS donor, *Brassica oleracea* breeding lines that are used as acceptor for the CMS trait (see FIG. 1).

b) Mitochondrial DNA composition

Figure 2:
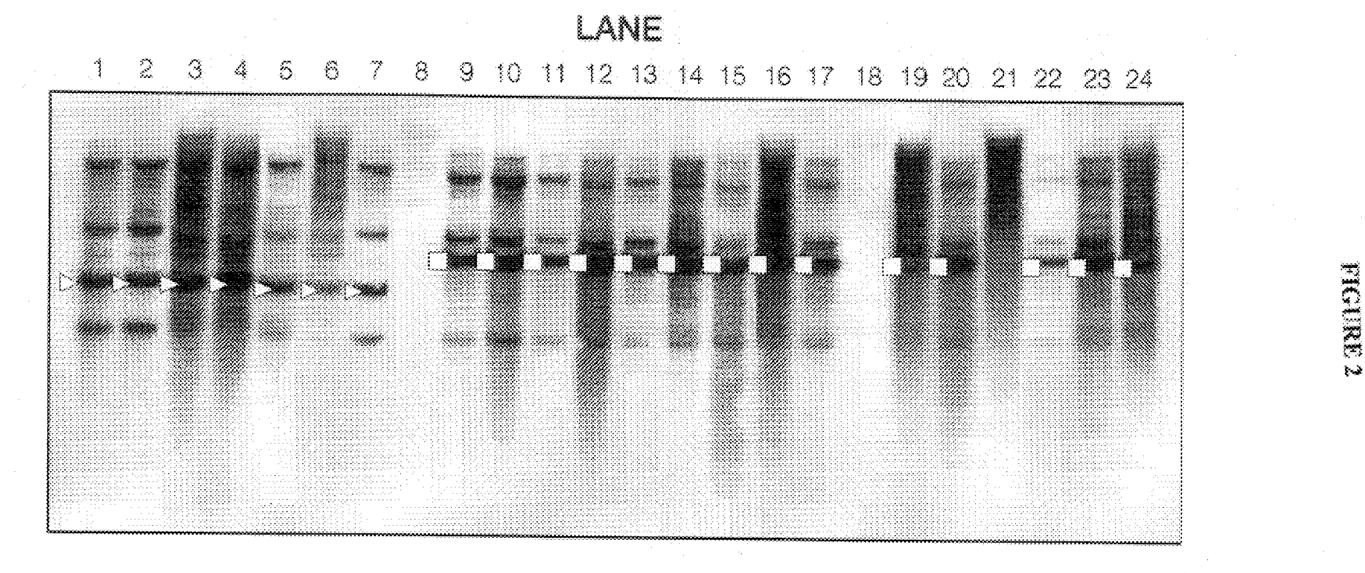
FIG. 2 shows the different hybridization patterns of BGLII digested DNA with probe CMS BRAS 4 in an endonuclease digest containing mitochondrial DNA of a polima CMS plant and mitochondrial DNA from an acceptor breeding line plant. Lanes 8 and 18 show Phage λ Hind III digested DNA fragments. Lanes 1 to 7 show Polima CMS *Brassica oleracea* 904005-1 DNA. Lanes 9 to 17 show *Brassica oleracea* acceptor Line K14. Lanes 19 to 24 show *Brassica oleracea* acceptor Line DE70.

Characterization is effected with CMS Bras 4 DNA, a clone containing a 1950 bp Bgl II fragment from cauliflower mitochondrial DNA. This clone produced a band of 4 kbp with CMS polima mitochondrial DNA and a band of 6 kbp with mitochondrial DNA from the acceptor breeding lines e.g. DE70 (see FIG. 2). Characterization is also effected by PCR amplification of a 500 bp DNA fragment, using primers 94RSO1 and 94RSO2. The sequence of the forward primer 94RSO1 is 5'-GAA CCA ACT GCT TTC ACA CCG-3' and of the reverse primer 94RSO2 5'-CTT GGC TCT CTG CGA ATG TC-3'. This 500 bp fragmnent is amplified from CMS polima mitochondrial DNA, but not from mitochondrial DNA of acceptor lines. e.g. DE70.

EXAMPLE 11
Embryo Rescue

Generally, an embryo is rescued 18–19 days after a cross is made. In order to effectuate an embryo rescue, siliques are required. The siliques required are those having as large as possible embryos with a seed coats that have not yet hardened.

Prior to the removal of the embryo, the siliques must first be disinfected. The siliques are disinfected by placing them in a 10% chloride solution such as sodium or potassium chloride for about twenty minutes (20 min.). The siliques are rinsed three times in sterile water at 2, 5 and 10 minutes.

The embryo is rescued by cutting the siliques open in a longitudinal direction, removing the developing seeds and then preparing the embryo out of the seed under a microscope.

After the embryo is cut out of the seed, it is placed on a suitable growth medium. Any medium that will facilitate the growth of the embryo can be used. For example, an MS medium with 3 & sucrose and 0.4 mg/l thiamin and 0.2 mg/l IDA can be used.

EXAMPLE 12
The maintenance of Sterility of CMS *Brassica oleracea* Plants at High and Low Temperatures In order to determine if the cytoplasmic male sterile plants containing the polima CMS cytoplasm remained sterile at high and low temperatures, broccoli cultivars 915095, 915107, 915100 and 915144 were hybridized with red cabbage to check if 100% hybridity was achieved. Cultivars 915095-915144 were crossed with red cabbage. When the seeds of these cultivars are pollinated with a normal broccoli maintainer and are sown, the hypocotyl color and leaf color of the seedling is normally green. If these cultivars are crossed with red cabbage then the hybrid seeds are intermediate and the seedlings show a strong anthocyanin (purple) expression, while inbreds remain green. Seeds of 915095, 915107, 915100, and 915144 were sown and 20 plants of each cultivar were put together with red cabbage plants in a plastic covered cage outside. In the summer, the temperature of the cage varied from 15–40° C. during the day. The temperatures in the cage were recorded once a week. A sample of the seed harvested from 915095, 915107, 915100 and 915144 were sown and all resulting plants were hybrid indicating no presence of selfing and no leaking of the polima CMS cytoplasm. At no time did any of the plants result in partial male sterility.

The crosses which lead to 915095, 915107, 915100 and 915144 are shown below.

When two or more arrows go from one cross (i.e. 88132× bc), then each arrow represents a cross with a different broccoli genotype.

EXAMPLE 13
Female Fertility

Listed below is the seed yield data obtained after crossing by hand CMS "Polima" types with broccoli. The data shows that the seed yield of CMS "polima" is higher than those of broccoli inbreds. This is because replicated inbreeding affects the fertility. A better comparison is made between the broccoli $F_1$'s and the CMS Ogura crosses. The results show that the seed yield of the CMS polima is in the same range as the other two types of crosses.

| Broccoli Seed Yields 1991–1994 (Hand pollination) | | |
| --- | --- | --- |
| Year | Type of Cross | Number of Seeds per Cross |
| 1991 | (CMS Polima × Broccoli) $F_1$ | 114 (n = 4) |
|  | (Broccoli inbred × Broccoli) $F_1$ | 64 (n = 23) |
|  | (Broccoli $F_1$ × Broccoli) $F_1$ | 116 (n = 45) |
| 1992 | (CMS Polima × Broccoli) $F_1$ | 146 (n = 66) |
|  | (Broccoli inbred × Broccoli) $F_1$ | 100 (n = 76) |
|  | (Broccoli $F_1$ × Broccoli) $F_1$ | 135 (n = 28) |
|  | (CMS Ogura × Broccoli) $F_1$ | 140 (n = 32) |
| 1993 | (CMS Polima × Broccoli) $F_1$ | 79 (n = 41) |

-continued

Broccoli Seed Yields 1991–1994 (Hand pollination)

| Year | Type of Cross | Number of Seeds per Cross |
|---|---|---|
|  | (Broccoli inbred × Broccoli) F$_1$ | 53 (n = 70) |
|  | (Broccoli F$_1$ × Broccoli) F$_1$ | 80 (n = 35) |
|  | (CMS Ogura × Broccoli) F$_1$ | 144 (n = 5) |
| 1994 | (CMS Polima × Broccoli) F$_1$ | 93 (n = 9) |
|  | (Broccoli inbred × Broccoli) F$_1$ | 47 (n = 50) |
|  | (Broccoli F$_1$ × Broccoli) F$_1$ | 84 (n = 35) |
|  | (CMS Ogura × Broccoli) F$_1$ | 74 (n = 9) |
| Weighted means |  |  |
|  | (CMS Polima × Broccoli) F$_1$ | 115 (n = 120) |
|  | (Broccoli inbred × Broccoli) F$_1$ | 60 (n = 227) |
|  | (Broccoli F$_1$ × Broccoli) F$_1$ | 103 (n = 143) |
|  | (CMS Ogura × Broccoli) F$_1$ | (127) ((n = 40)) |

Although the invention has been described primarily in connection with the special and preferred embodiments, it will be understood that it is capable of modification without departing from the scope of the invention. The following claims are intended to cover all variations, uses or adaptions of the invention, following, in general, the principles thereof and including such departures from the presented disclosure as come within known or customary practice in the field to which the invention pertains, or as are obvious to persons skilled in the field.

We claim:

1. A method for producing cytoplasmic male sterile *Brassica oleracea* plants which are sterile at high and low temperature and which contain polima CMS cytoplasm, the method comprising the steps of:
    a) crossing *Brassica campestris* cultivar 87110 having ATCC Accession Number 97246 with *Brassica oleracea* cultivar 87101 and collecting and seeds resulting from said cross;
    b) regenerating said seeds into *Brassica napus* plants which contain a haploid set of chromosomes;
    c) doubling the chromosomes of the plants of step b to provide *Brassica napus* plants containing a diploid set of chromosomes;
    d) crossing *Brassica campestris* cultivar 87118 having ATCC Accession Number 97247 with *Brassica oleracea* cultivar 87101 and collecting the seeds resulting from said cross;
    e) regenerating said seeds of step d into *Brassica napus* plants which contain a haploid set of chromosomes;
    f) doubling the chromosomes of the plants of step e to provide *Brassica napus* plants containing a diploid set of chromosomes;
    g) crossing the plants of step f with *Brassica napus* cultivar 87102 which is male sterile and contains polima CMS cytoplasm and collecting the seeds resulting from said cross;
    h) regenerating said seeds of step g into *Brassica napus* plants containing the polima CMS cytoplasm;
    i) crossing the plants of step c with the plants of step h and collecting the seeds resulting from said cross;
    j) regenerating said seeds of step i into *Brassica napus* plants which are male sterile and contain the polima CMS cytoplasm;
    k) crossing the plants of step j with a *Brassica oleracea* cultivar and collecting the seeds resulting from said cross;
    l) removing the embryos from the seeds of step k and regenerating said embryos into F$_1$ plants which are male sterile and contain the polima CMS cytoplasm;
    m) backcrossing the plants from step l with a *Brassica oleracea* cultivar and collecting the seeds resulting from said backcrossing;
    n) removing the embryos from the seeds of step m and regenerating said embryos into plants which are male sterile and contain the polima CMS cytoplasm;
    o) backcrossing the plants from step n with a *Brassica oleracea* and collecting the seeds resulting from said backcrossing; and
    p) regenerating said seeds of step o into *Brassica oleracea* plants which are male sterile at high and low temperatures and contain the polima CMS cytoplasm.

2. The method of claim 1 further comprising the steps of crossing the plants from step p with a *Brassica oleracea*; collecting seeds resulting from the cross; and regenerating said seeds into *Brassica oleracea* plants which are male sterile and contain the polima CMS cytoplasm.

3. The method of claim 1 wherein the *Brassica oleracea* plants of step p are selected from the group consisting of: cauliflower (*B. oleracea* L. convar. botrytis (L.) Alef. var. botrytis L.), brussel sprouts (*B. oleracea* L. convar. oleracea var. gemmifera DC.), white cabbage (*B. oleracea* L. convar. capitata (L.) Alef. var. alba DC), oxheart cabbage (*B. oleracea* L. convar. capitata (L.) Alef. var. alba DC.), red cabbage (*B. oleracea* L. convar. capitata (L.) Alef. var. rubra DC.), savoye cabbage (*B. oleracea* L. convar. capitata (L.) Alef. var. sabauda L.), turnip cabbage (*B. oleracea* L. convar. acephala DC.) Alef. var. sabellica L.), portugese cabbage (*B. oleracea*. var. tronchuda syn. costata), curly kale cabbage (*B. oleracea* L. convar. acephala (DC.) Alef. var. sabellica L.), kohlrabi (*Brassica oleracea* L. convar. acephala (DC.) Alef. var. gongylodes L.), and broccoli (*B. oleracea* L. convar. botrytis (L.) Alef. var. cymosa Duch.).

4. A method for producing cytoplasmic male sterile *Brassica oleracea* plants which are male sterile at high and low temperatures and which contain polima CMS cytoplasm; the method comprising the steps of:
    a) fusing a protoplast from a male sterile *Brassica oleracea* produced according to the method of claim 1 which contains the polima CMS cytoplasm and which remains sterile at high and low temperatures with a protoplast from a *Brassica oleracea* having commercially desirable characteristics to produce allogenic cells; and
    b) regenerating the obtained allogenic cells into CMS *Brassica oleracea* plants which are sterile at high and low temperatures and which contain polima cytoplasm.

5. The method of claim 4 wherein the *Brassica oleracea* plants of step b are selected from the group consisting of: cauliflower (*B. oleracea* L. convar. botrytis (L.) Alef. var. botrytis L.), brussel sprouts (*B. oleracea* L. convar. oleracea var. gemmifera DC.), white cabbage (*B. oleracea* L. convar. capitata (L.) Alef. var. alba DC.), oxheart cabbage (*B. oleracea* L. convar. capitata (L.) Alef. var. alba DC.), red cabbage (*B. oleracea* L. convar. capitata (L.) Alef. var. rubra DC.), savoye cabbage (*B. oleracea* L. convar. capitata (L.) Alef. var. sabauda L.), turnip cabbage (*B. oleracea* L. convar. acephala DC.) Alef. var. sabellica L.), portugese cabbage (*B. oleracea*. var. tronchuda syn. costata), curly kale cabbage (*B. oleracea* L. convar. acephala (DC.) Alef. var. sabellica L.), kohlrabi (*Brassica oleracea* L. convar. acephala (DC.) Alef. var. gongylodes L.), and broccoli (*B. oleracea* L. convar. botyrytis (L.) Alef. var. cymosa Duch.).

6. The method of claim 4 further comprising the steps of crossing the regenerated CMS *Brassica oleracea* containing polima cytoplasm with *Brassica oleracea* plants containing commercially desirable characteristics.

7. Cytoplasmic male sterile *Brassica oleracea* plants produced by the method of claim 1 which are sterile at high and low temperatures and contain Polima CMS cytoplasm.

8. Cytoplasmic male sterile *Brassica oleracea* plants produced by the method of claim 4 which are sterile at high and low temperatures and contain Polima CMS cytoplasm.

9. The plants of claims 7 or 8 wherein the plants are selected from the group consisting of: cauliflower, brussels sprouts, cabbage, kale, kohlrabi, and broccoli.

10. The method of claim 4 wherein the protoplast from the male sterile *Brassica oleracea* contains inactivated nuclei.

11. Seeds produced from the plants of claim 7.

12. Seeds produced from the plants of claim 8.

* * * * *